US012758425B2

(12) United States Patent
Bor et al.

(10) Patent No.: US 12,758,425 B2
(45) Date of Patent: Oct. 13, 2026

(54) SLO-BASED LASER GUIDANCE FOR TREATING VITREOUS FLOATERS

(71) Applicant: Alcon Inc., Fribourg (CH)

(72) Inventors: Zsolt Bor, San Clemente, CA (US); Alireza Malek Tabrizi, Irvine, CA (US)

(73) Assignee: Alcon Inc., Fribourg (CH)

( * ) Notice: Subject to any disclaimer, the term of this patent is extended or adjusted under 35 U.S.C. 154(b) by 652 days.

(21) Appl. No.: 18/296,647

(22) Filed: Apr. 6, 2023

(65) Prior Publication Data

US 2023/0320900 A1 Oct. 12, 2023

Related U.S. Application Data

(60) Provisional application No. 63/330,141, filed on Apr. 12, 2022.

(51) Int. Cl.
*A61F 9/008* (2006.01)

(52) U.S. Cl.
CPC *A61F 9/00825* (2013.01); *A61F 2009/00846* (2013.01); *A61F 2009/00874* (2013.01); *A61F 2009/00897* (2013.01)

(58) Field of Classification Search
CPC ........ A61F 9/00825; A61F 2009/00846; A61F 2009/00874; A61F 2009/00897
See application file for complete search history.

(56) References Cited

U.S. PATENT DOCUMENTS 3,780,979 A 12/1973 De Guillebon
4,357,088 A 11/1982 Pomerantzeff
(Continued)

FOREIGN PATENT DOCUMENTS

AU 2018274939 B2 6/2020
CN 210009227 U 2/2020
(Continued)

OTHER PUBLICATIONS

Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.
(Continued)

*Primary Examiner* — Lynsey C Eiseman
*Assistant Examiner* — Skylar Lindsey Christianson
(74) *Attorney, Agent, or Firm* — Patterson + Sheridan, LLP

(57) ABSTRACT

In certain embodiments, an ophthalmic surgical laser system for imaging and treating an eye floater includes an SLO subsystem, a treatment laser subsystem, a scanner, optical elements, and a computer. The SLO subsystem provides an SLO laser beam with an SLO focal point, and the treatment laser subsystem provides a treatment laser beam with a treatment focal point that spatially coincides with the SLO focal point. The scanner scans the SLO laser beam across a scan region and directs the treatment laser beam to the xy-location of the scan region. The optical elements aim the SLO laser beam and the treatment laser beam at substantially the same point of the scan region. The computer receives an SLO image of the floater, determines an xy-location of the floater, and instructs the treatment laser subsystem to direct the treatment laser beam towards the xy-location and the z-scan location of the floater.

24 Claims, 9 Drawing Sheets

(56) References Cited

U.S. PATENT DOCUMENTS

| | | | | |
|---|---|---|---|---|
| 5,312,396 | A | 5/1994 | Feld | |
| 5,909,270 | A | 6/1999 | Moser | |
| 6,142,630 | A | 11/2000 | Koester | |
| 6,322,556 | B1 | 11/2001 | Gwon | |
| 6,789,900 | B2 | 9/2004 | Van De Velde | |
| 7,374,287 | B2 | 5/2008 | Van De Velde | |
| 7,510,282 | B2 | 3/2009 | Ueno | |
| 7,520,613 | B2 | 4/2009 | Saito et al. | |
| 7,703,922 | B2 | 4/2010 | Van De Velde | |
| 8,480,659 | B2 | 7/2013 | Frey et al. | |
| 8,652,602 | B1 | 2/2014 | Dolla | |
| 8,783,868 | B2 | 7/2014 | Qiu | |
| 8,876,808 | B2 | 11/2014 | Feklistov et al. | |
| 8,994,753 | B2 | 3/2015 | Nakano | |
| 9,033,500 | B2 | 5/2015 | Utsunomiya | |
| 9,603,519 | B2 | 3/2017 | Bor et al. | |
| 9,675,243 | B2 | 6/2017 | Sasak et al. | |
| 9,789,002 | B2 | 10/2017 | Van De Velde | |
| 10,130,511 | B2 | 11/2018 | Dantus | |
| 10,478,342 | B2 | 11/2019 | Dick | |
| 10,555,835 | B2 | 2/2020 | Schuele et al. | |
| 2003/0179344 | A1* | 9/2003 | Van de Velde | A61F 9/00821 351/200 |
| 2007/0258094 | A1 | 11/2007 | Izatt et al. | |
| 2007/0291277 | A1 | 12/2007 | Everett | |
| 2009/0073384 | A1 | 3/2009 | Warden | |
| 2009/0137989 | A1 | 5/2009 | Kataoka | |
| 2009/0196477 | A1 | 8/2009 | Cense et al. | |
| 2010/0123873 | A1 | 5/2010 | Raymond | |
| 2010/0152847 | A1 | 6/2010 | Padrick | |
| 2011/0077557 | A1 | 3/2011 | Wing et al. | |
| 2012/0281235 | A1 | 11/2012 | Murata | |
| 2013/0131652 | A1 | 5/2013 | Dick | |
| 2013/0173029 | A1 | 7/2013 | Caldeira et al. | |
| 2013/0194548 | A1* | 8/2013 | Francis | A61B 3/15 351/208 |
| 2014/0058367 | A1 | 2/2014 | Dantus | |
| 2014/0216468 | A1 | 8/2014 | Goldshleger | |
| 2014/0257257 | A1 | 9/2014 | Grant et al. | |
| 2014/0268036 | A1 | 9/2014 | Ketterling et al. | |
| 2014/0276674 | A1 | 9/2014 | Lee | |
| 2015/0190278 | A1 | 7/2015 | Gooding | |
| 2015/0342782 | A1 | 12/2015 | Mordaunt | |
| 2016/0058617 | A1 | 3/2016 | Uttrull et al. | |
| 2016/0074214 | A1 | 3/2016 | Palanker et al. | |
| 2016/0074221 | A1* | 3/2016 | Tassignon | G06F 16/24 606/4 |
| 2016/0166431 | A1 | 6/2016 | Vogler et al. | |
| 2016/0227999 | A1 | 8/2016 | An et al. | |
| 2016/0235588 | A1 | 8/2016 | Hart et al. | |
| 2016/0256324 | A1 | 9/2016 | Suzuki | |
| 2016/0278629 | A1 | 9/2016 | Schuele | |
| 2016/0302969 | A1 | 10/2016 | Yamamoto | |
| 2017/0181625 | A1 | 6/2017 | Kawakami et al. | |
| 2017/0252213 | A1 | 9/2017 | Furuuchi et al. | |
| 2017/0326003 | A1 | 11/2017 | Schuele et al. | |
| 2018/0028354 | A1 | 2/2018 | Heeren | |
| 2018/0028355 | A1 | 2/2018 | Raksi | |
| 2018/0140257 | A1 | 5/2018 | Govindjee et al. | |
| 2018/0206719 | A1 | 7/2018 | Adler et al. | |
| 2018/0353064 | A1 | 12/2018 | Soetikno et al. | |
| 2018/0368915 | A1 | 12/2018 | Xia et al. | |
| 2019/0159933 | A1 | 5/2019 | Romano et al. | |
| 2019/0282403 | A1 | 9/2019 | Barrett et al. | |
| 2019/0290124 | A1 | 9/2019 | Laforest et al. | |
| 2019/0313903 | A1 | 10/2019 | Mckinnon | |
| 2019/0365569 | A1 | 12/2019 | Skovgaard | |
| 2020/0038241 | A1 | 2/2020 | Wang et al. | |
| 2020/0060873 | A1 | 2/2020 | Heeren | |
| 2020/0069463 | A1* | 3/2020 | Chen | A61F 9/008 |
| 2020/0085292 | A1 | 3/2020 | Fukuma et al. | |
| 2020/0129336 | A1 | 4/2020 | Schuele et al. | |
| 2020/0130103 | A1 | 4/2020 | Choi | |
| 2020/0192080 | A1 | 6/2020 | Karam | |
| 2020/0196853 | A1 | 6/2020 | Van Hemert et al. | |
| 2020/0273218 | A1 | 8/2020 | Camino et al. | |
| 2020/0397289 | A1 | 12/2020 | Ralston | |
| 2020/0400422 | A1 | 12/2020 | Ralston | |
| 2021/0100450 | A1 | 4/2021 | Amma | |
| 2021/0186753 | A1 | 6/2021 | Al-Qaisi et al. | |
| 2021/0275009 | A1 | 9/2021 | Yates | |
| 2021/0353141 | A1* | 11/2021 | Moon | A61B 3/103 |
| 2021/0378507 | A1 | 12/2021 | Wallace | |
| 2021/0386586 | A1 | 12/2021 | Bor | |
| 2022/0012459 | A1 | 1/2022 | Schwiegerling | |
| 2022/0031511 | A1 | 2/2022 | Charles | |
| 2023/0157889 | A1 | 5/2023 | Bor | |

FOREIGN PATENT DOCUMENTS

| | | | |
|---|---|---|---|
| CN | 108371542 | B | 4/2020 |
| CN | 109196333 | B | 12/2020 |
| CN | 111281651 | B | 12/2020 |
| CN | 112862782 | A | 5/2021 |
| CN | 112587302 | B | 6/2021 |
| CN | 112587304 | B | 6/2021 |
| DE | 19705044 | A1 | 8/1998 |
| DE | 102019007147 | A1 | 4/2021 |
| DE | 102019007148 | A1 | 4/2021 |
| EP | 0770370 | A2 | 2/1997 |
| EP | 1212022 | B1 | 3/2005 |
| EP | 1563785 | A1 | 8/2005 |
| EP | 1638452 | B1 | 10/2006 |
| EP | 1838212 | A1 | 10/2007 |
| EP | 2144552 | A1 | 1/2010 |
| EP | 1928297 | B1 | 11/2010 |
| EP | 2459138 | A2 | 6/2012 |
| EP | 2525706 | A2 | 11/2012 |
| EP | 2898820 | A1 | 7/2015 |
| EP | 3061429 | A1 | 8/2016 |
| EP | 2890340 | B1 | 2/2017 |
| EP | 3459487 | A1 | 3/2019 |
| EP | 3501463 | A1 | 6/2019 |
| EP | 3636137 | A1 | 4/2020 |
| EP | 3861924 | A1 | 8/2021 |
| GB | 2469249 | A | 10/2010 |
| JP | 5767014 | B2 | 6/2015 |
| JP | 2017176558 | A | 10/2017 |
| JP | 6410468 | B2 | 10/2018 |
| JP | 2018196821 | A | 12/2018 |
| JP | 2018196822 | A | 12/2018 |
| JP | 2020022569 | A | 2/2020 |
| JP | 6736304 | B2 | 7/2020 |
| JP | 6839902 | B2 | 2/2021 |
| RU | 2661016 | C1 | 7/2018 |
| RU | 2692666 | C1 | 6/2019 |
| RU | 2695629 | C1 | 7/2019 |
| RU | 2710058 | C2 | 12/2019 |
| RU | 2726468 | C1 | 7/2020 |
| WO | 9958047 | A1 | 11/1999 |
| WO | 0137769 | A1 | 5/2001 |
| WO | 0195791 | A1 | 12/2001 |
| WO | 2007059189 | A2 | 5/2007 |
| WO | 2009033110 | A2 | 3/2009 |
| WO | 2009036104 | A2 | 3/2009 |
| WO | 2009039315 | A2 | 3/2009 |
| WO | 2009059400 | A1 | 5/2009 |
| WO | 2010117386 | A1 | 10/2010 |
| WO | 2014053824 | A1 | 4/2014 |
| WO | 2015131135 | A1 | 9/2015 |
| WO | 2015171793 | A1 | 11/2015 |
| WO | 2016033590 | A1 | 3/2016 |
| WO | 2017062673 | A1 | 4/2017 |
| WO | 2017196306 | A1 | 11/2017 |
| WO | 2017205857 | A1 | 11/2017 |
| WO | 2020074532 | A1 | 4/2020 |
| WO | 2020180729 | A1 | 9/2020 |
| WO | 2020215359 | A1 | 10/2020 |
| WO | 2020216763 | A1 | 10/2020 |
| WO | 2020257711 | A1 | 12/2020 |
| WO | 2021023799 | A1 | 2/2021 |
| WO | 2021049243 | A1 | 3/2021 |
| WO | 2021066047 | A1 | 4/2021 |
| WO | 2021092211 | A1 | 5/2021 |

(56) References Cited

FOREIGN PATENT DOCUMENTS

| | | | |
|---|---|---|---|
| WO | 2021183637 | A1 | 9/2021 |
| WO | 2022149028 | A1 | 7/2022 |
| WO | 2023089416 | A1 | 5/2023 |
| WO | 2023089459 | A1 | 5/2023 |
| WO | 2023097391 | A1 | 6/2023 |

OTHER PUBLICATIONS

Chirag P. Shah, et al., YAG Laser Vitreolysis vs Sham YAG Vitreolysis for Symptomatic Vitreous Floaters A Randomized Clinical Trial, JAMA Ophthalmology, Sep. 2017, 918-923, 135-9.

Damodaran et al., "Digital micromirror device based ophthalmoscope with concentric circle scanning", 2017, pp. 2766-2780, vol. 8, No. 5, Biomedical Optics Express.

Ellex Website, Treatment Guidelines—Laser Floater Removal; 2016, Ellex Medical Pty Ltd. E&OE. VB0002E, downloaded Apr. 20, 2017.

Felix Sauvage et al: "Photoablation of Human Vitreous Opacities by Light-Induced Vapor Nanobubbles", ACS Nano, vol. 13, No. 7, Jul. 9, 2019, pp. 8401-8416.

Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.

Ginner et al., "Wide-Field OCT Angiography at 400 KHz Utilizing Spectral Splitting", Photonics, Oct. 23, 2014, pp. 369-379, vol. 1, No. 4.

Heidelberg Engineering GmbH, "Spectralis. Hardware Operating Instructions," Version 001, Aug. 2007.

Heidelberg Engineering, "Spectralis. Multimodal Imaging Platform Optimized for the Posterior Segment", accessed on Jan. 30, 2023 from https://business-lounge.heidelbergengineering.com/us/en/products/spectralis/spectralis/.

Hofer et al., "Dispersion encoded full range frequency domain optical coherence tomography", Jan. 5, 2009, pp. 7-24, vol. 17, No. 1, Optics Express, US.

Hofer et al., "Fast dispersion encoded full range optical coherence tomography for retinal imaging at 800 nm and 1060 nm", Mar. 1, 2010, pp. 4898-4919, vol. 18, No. 5, Optics Express.

Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.

Leitgeb et al., "Complex ambiguity-free Fourier domain optical coherence tomography through transverse scanning", 2007, pp. 3453-3455, vol. 32, Optics Letters.

Li et al., "DMD-based three-dimensional chromatic confocal microscopy", 2020, pp. 4349-4356, vol. 59, No. 14, Applied Optics.

Martial et al., "Programmable Illumination and High-Speed, Multi-Wavelength, Confocal Microscopy Using a Digital Micromirror", Aug. 2012, e43942, vol. 7, No. 8, PLOS ONE.

Michael J. Escuti, et al., "Geometric-Phase Holograms", Optics & Photonics News, pp. 22-29, Feb. 2016.

Milston Rebecca et al: "Vitreous floaters: Etiology, diagnostics, and management", Survey of Ophthalmology, vol. 61, No. 2, Mar. 1, 2016, pp. 211-227.

Nicusor Iftimia et al: "Hybrid retinal imaginer using line-scanning laser ophthalmoscopy and spectral domain optical coherence tomography", Optics Express, vol. 14, No. 26, Dec. 22, 2006.

Reece Bergstrom, et al., Vitreous Floaters, National Center for Biotechnology Information, May 21, 2020, 4 pages, Bookshelf ID NBK470420, StatPearls Publishing LLC, online.

Reznicek Lukas et al., "Wide-Field Megahertz OCT Imaging of Patients with Diabetic Retinopathy", Journal of Diabetes Research, 2015, 5 pages.

Ruggeri et al., "Imaging and full-length biometry of the eye during accommodation using spectral domain OCT with an optical switch", Jul. 1, 2012, pp. 1506-1520, vol. 3, No. 7, Biomedical Optics Express.

Sarunic et al., "Instantaneous complex conjugate resolved spectral domain and swept-source OCT using 3×3 fiber couplers", Feb. 2005, pp. 957-967, vol. 13, No. 3, Optics Express.

Shields et al., "Wide-angle Imaging of the Ocular Fundus", Review of the Ophthalmology, Feb. 15, 2003.

Singh, "Lasers Take Aim at Floaters", Ophthalmology Management, Jul. 1, 2019, pp. 38, 40-42, 59, vol. 23.

Singh, "Modern vitreolysis—YAG laser treatment now a real solution for the treatment of symptomatic floaters", Survey of Ophthalmology, Mar. 3, 2020, pp. 581-591, vol. 65, No. 5.

SunLED, NanoPoint-0201 Series LEDs, published Feb. 15, 2016, www.SunLEDusa.com.

Volk Optical, "Volk Idrees Mid-Vitreous Lens", Dec. 20, 2020, accessed on Dec. 20, 2020 from https://www.volk.com/...s?pr_prod_strat-collection_fallback&pr_rec_pid=4513049018402&pr_ref_pid=4513048952866&pr_seq=uniform.

Volk Optical, "Volk Singh Mid-Vitreous Lens", Dec. 20, 2020, accessed on Dec. 20, 2020 from https://www.volk.com/products/singh-mid-vitreous-vitreous-slit-lamp-lens?_pos=3&_sid=b50c0674f&_ss=r.

Wang et al., "In vivo full range complex Fourier domain optical coherence tomography", Jan. 30, 2007, 054103, vol. 90, Applied Physics Letters.

Wikipedia Encyclopedia, Floater, Wikipedia Encyclopedia, Mar. 29, 2021, online: https://en.wikipedia.org/wiki/rloater?wprov=sfti 1.

Wojtkowski et al., "Full range complex spectral optical coherence tomography technique in eye imaging", 2002, pp. 1415-1417, vol. 27, No. 16, Optics Letters.

Yasuno et al., "Simultaneous B-M-mode scanning method for real-time full-range Fourier domain optical coherence tomography", 2006, pp. 1861-1865, vol. 45, No. 8, Applied Optics.

Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.

Zhang Yunbo et al: "Parallel large-range scanning confocal microscope based on a digital micromirror device", Optik vol. 124, No. 13 (2013), Aug. 4, 2012, pp. 1585-1588.

Zhou et al., "Dual channel dual focus optical coherence tomography for imaging accommodation of the eye", May 25, 2009, pp. 8947-8955, vol. 17, No. 11, Optics Express.

Adrian G.H. Podoleanu et al., Combined optical coherence tomograph and scanning laser ophthalmoscope mi nije dostupan besplatno., Electronics Letters, 34 (11), 1998.

Chi-Hung Lee, et al., Imaging vitreous floaters and cataracts with optical simulations, Optik, 194, 1-9, 2019.

Christy K. Sheehy et al., High-speed, image-based eye tracking with a scanning laser ophthalmoscope, Biomedical Optics Express, vol. 3, No. 10, 2012.

D. H. Kelly, "Retinal Inhomogeneity. II. Spatial Summation," J. Opt. Soc. Am., pp. 114-119, vol. 1, No. 1 (Jan. 1984).

D. H. Kelly, "Retinal Inhomogeneity. III. Circular—Retina Theory," D.H. Kelly, J. Opt. Soc. Am., pp. 810-819, vol. 2, No. 6 (Jun. 1985).

D.H. Kelly, "Visual Processing of Moving Stimuli," J. Opt. Soc. Am., pp. 216-225, vol. 2, No. 2 (Feb. 1985).

D.H. Kelly,, "Motion and Vision. II. Stabilized Spatio-Temporal Threshold Surface," J. Opt. Soc. Am., pp. 1340-1349, vol. 69, No. 10 (Oct. 1979).

D.H.Kelly, "Retinal Inhomogeneity. I. Spatiotemporal Contrast Sensitivity," J. Opt. Sec. Am., pp. 107-113, vol. 1, No. 1 (Jan. 1984).

Mojana F. et al.. Observations by spectral-domain optical coherence tomography combined with simultaneous scanning laser ophthalmoscopy: imaging of the vitreous, American Journal of Ophthalmol. Apr. 2010;149(4):641-650.

Nidek, Scanning Laser Ophthalmoscope Mirante SLO/OCT Mirante SLO, https://www.nidek-intl.com/product/ophthaloptom/diagnostic/dia_retina/mirante.htm.

(56) References Cited

OTHER PUBLICATIONS

Peter G. J. Barten, "Contrast Sensitivity of the Human Eye and its Effects on Image Quality," Chapter 3, pp. 27-40, Model for the spatial contrast sensitivity of the eye, (1999).
Pointer, J. S., & Hess, R. F. "The contrast sensitivity gradient across the human visual field: With emphasis on the low spatial frequency range,", R. F. Vision Research, 29(9), 1133-1151 (1989).
Sebag J et al., Vitreous and Vitreoretinal Interface, Ch. 21, 2015.
Sebag J., Vitreous and Vision Degrading Myodesopsia. Progress in Retinal and Eye Research Nov. 2020;79.
T Ivanova et al, Vitrectomy for primary symptomatic vitreous opacities: an evidence-based review, Eye (Lond) May 2016;30(5):645-55.
Teri T Kleinberg et al., Vitreous substitutes: a comprehensive review, Survey of Ophthalmology, 56 (4), 2011.

* cited by examiner

SLO-BASED LASER GUIDANCE FOR TREATING VITREOUS FLOATERS

TECHNICAL FIELD

The present disclosure relates generally to ophthalmic surgical laser systems, and more particularly to confocal SLO-based laser guidance for treating vitreous floaters.

BACKGROUND

Eye floaters are clumps of collagen proteins that form in the vitreous. These clumps can disturb vision with moving shadows. In laser vitreolysis, a laser beam is directed into the vitreous to fragment the floaters to improve vision.

BRIEF SUMMARY

In certain embodiments, an ophthalmic surgical laser system for treating a floater in a vitreous of an eye includes a scanning laser ophthalmoscope (SLO) subsystem, a treatment laser subsystem, a scanner, optical elements (including focusing lenses), and a computer. The SLO subsystem includes an SLO laser source and a pinhole filter. The SLO laser source provides an SLO laser beam with an SLO focal point, and the pinhole filter is conjugated to the SLO focal point. The treatment laser subsystem provides a treatment laser beam with a treatment focal point that spatially coincides with the SLO focal point. The scanner scans the SLO laser beam across a scan region and directs the treatment laser beam to the xy-location of the scan region. The optical elements aim the SLO laser beam and the treatment laser beam at substantially the same point of the scan region, focus the SLO focal point to form the scan region at a z-scan location, move the scan region to the z-scan location of the floater, and focus the treatment focal point at the z-scan location of the floater. The computer receives an image of the floater from the SLO subsystem, determines an xy-location of the floater, and instructs the treatment laser subsystem to direct the treatment laser beam towards the xy-location and the z-scan location of the floater.

Embodiments may include none, one, some, or all of the following features:

- The optical elements move the scan region in the z-direction by changing the relative distance between the eye and at least one optical element.
- The optical elements move the scan region in the z-direction by changing the relative distance between the focusing lenses.
- The ophthalmic surgical laser system includes a tunable lens that moves the SLO focal point and the treatment focal point. The optical elements move the scan region in the z-direction by adjusting the tunable lens to move the SLO focal point and the treatment focal point.
- The computer determines the xy-location of the floater by receiving user input indicating the xy-location of the floater.
- The computer determines the xy-location of the floater by analyzing the image of the floater from the SLO subsystem and determining the xy-location of the floater from the image.
- The optical elements move the scan region to the retina of the eye, and the SLO subsystem generates an image of a shadow of the floater on the retina.
- The treatment laser subsystem directs the treatment laser beam towards the xy-location and the z-scan location of the floater by directing a laser pulse at the floater.

- The treatment laser subsystem directs the treatment laser beam towards the xy-location and the z-scan location of the floater by directing laser pulses towards the floater to form a three-dimensional volume covering 80% or more of the volume of the floater.
- The computer analyzes an image of a shadow on the retina of the eye from the SLO subsystem and determines whether the shadow is cast by a significant floater.
- The computer analyzes an image of the floater from the SLO subsystem and determines whether the floater is in focus.
- The computer calculates a floater-to-retina distance according to changes in the system used to adjust the scan region between the retina and the floater. The computer may calculate the floater-to-retina distance according to the distance system components move to adjust the scan region between the retina and the floater, or according to the difference in diopters used to adjust the scan region between the retina and the floater.
- The computer calculates a retinal radiation exposure of the treatment laser beam focused at the z-scan location of the floater, and performs an alarm response if the retinal radiation exposure exceeds a predetermined limit. The computer may calculate the retinal radiation exposure EXP according to $EXP=E/[(L*\alpha)^2\pi/4]$, where E represents a laser pulse energy, $\alpha$ represents a full convergence angle of the treatment laser beam focused at the z-scan location of the floater, and L represents a floater-to-retina distance calculated according to the z-scan location of the floater.
- The computer tracks movement of the floater using tracking software.
- The SLO subsystem generates images of the eye at different z-scan locations, and the computer generates a three-dimensional image from the images.
- The system further comprises a display. The display may be a computer monitor or virtual reality glasses.
- The treatment laser beam has a wavelength in the range of 350 nanometers (nm) to 2000 nm and laser pulses with pulse durations in the range of 20 femtoseconds (fs) to 1000 nanoseconds (ns).
- The system further comprises an ultrasonic sensor that monitors the position of the eye and/or head of the patient relative to an objective lens.

In certain embodiments, a method for treating a floater in a vitreous of an eye includes: providing, by a scanning laser ophthalmoscope (SLO) subsystem, an SLO laser beam with an SLO focal point; providing, by a treatment laser subsystem, a treatment laser beam with a treatment focal point, the treatment focal point spatially coinciding with the SLO focal point; scanning, by a scanner, the SLO laser beam across a scan region; aiming, by optical elements, the SLO laser beam and the treatment laser beam at substantially the same point of the scan region; focusing, by the optical elements, the SLO focal point to form the scan region at a z-scan location; moving, by the optical elements, the scan region to the z-scan location of the floater; receiving, by a computer, an image of the floater from the SLO subsystem; determining, by the computer, an xy-location of the floater; instructing, by the computer, the treatment laser subsystem to direct the treatment laser beam towards the xy-location and the z-scan location of the floater; directing, by the scanner, the treatment laser beam to an xy-location of the scan region; and focusing, by the optical elements, the treatment focal point at the z-scan location of the floater.

Embodiments may include none, one, some, or all of the following features:

The scan region is moved in the z-direction by changing the relative distance between the eye and at least one optical element.

The scan region is moved in the z-direction by changing the relative distance between the focusing lenses.

The scan region is moved in the z-direction by adjusting a tunable lens to move the SLO focal point and the treatment focal point.

DESCRIPTION OF EXAMPLE EMBODIMENTS

Figure 1A:
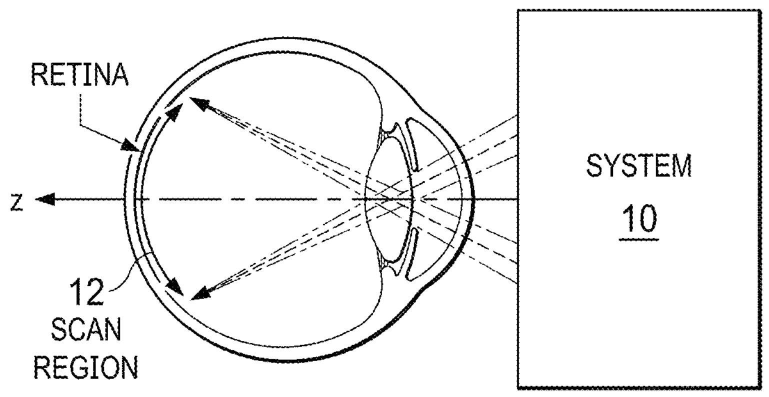
FIGS. 1A and 1B illustrate an example of an ophthalmic surgical laser system that can move a scan region to different z-locations.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In certain laser vitreolysis systems, an OCT device is used to provide the z-location of a floater to guide a treatment laser beam towards the floater. OCT devices, however, are complex and expensive. Accordingly, embodiments described herein do not use an OCT device to provide the z-location of the floater.

Examples of a system described herein provide a scanning laser ophthalmoscope (SLO) laser beam to generate an SLO image of a floater or a retinal floater shadow and a treatment laser beam to disintegrate the floater. The system collimates and aligns both the SLO and treatment laser beams, so the focal points of the beams are focused and aimed at the substantially the same location within the eye. In the embodiments, the focal point of the SLO laser beam can be moved in the z-direction to image the floater itself. When the floater image is in focus, the treatment beam is also focused on the floater since the SLO and treatment focal points are aimed at the same location. Thus, an SLO device can be used to direct a treatment beam towards the z-location of a floater, without assistance from an OCT device.

1. Example Surgical System

Figure 1B:
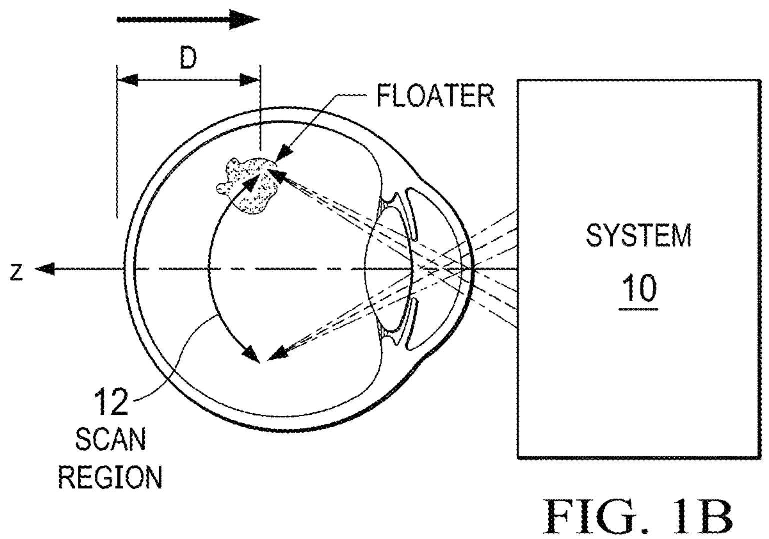
Figure 2B:
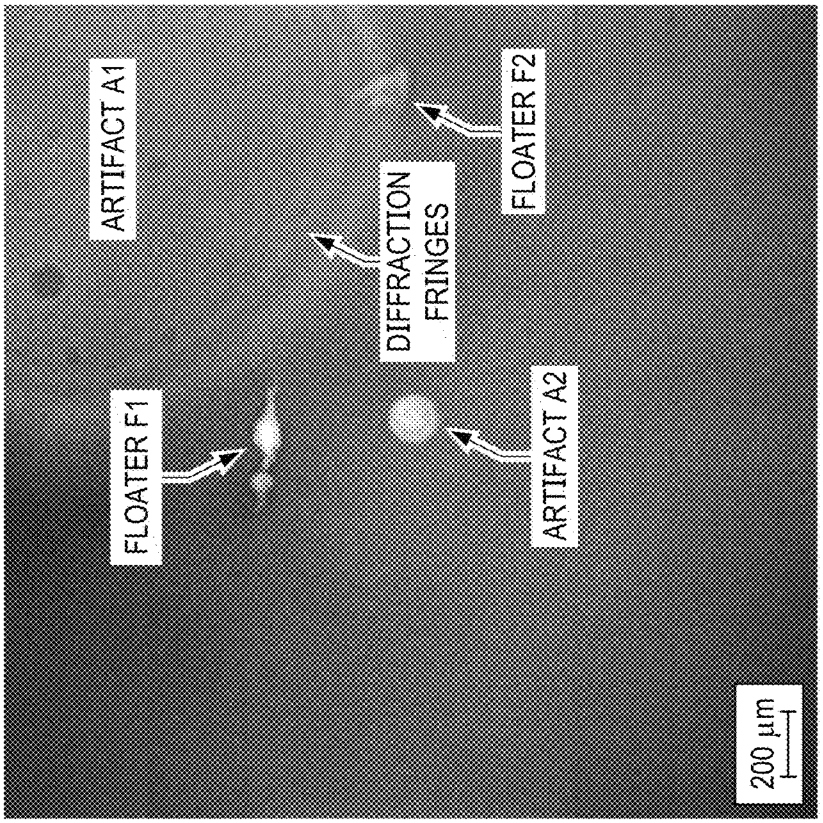
FIGS. 2A through 2C illustrate examples of images that may be generated at different z-locations.
Figure 2A:
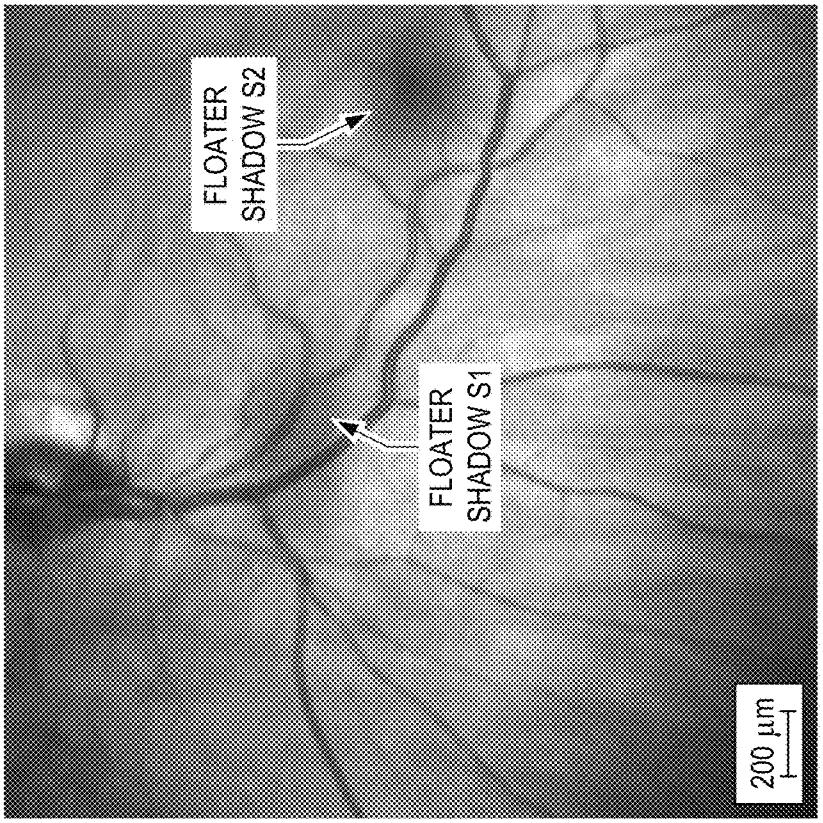

FIGS. 1A and 1B illustrate an example of an ophthalmic surgical laser system 10 that can move a scan region 12 to different z-locations, e.g., from the retina to a floater, and FIGS. 2A and 2B illustrate examples of SLO images that may be generated at the different z-locations. Scan region 12 is the focal surface indicating where the focal points of SLO and treatment laser beams are aimed. In the example, the z-location of scan region 12 may be described as the "z-scan location". For example, the z-scan location of scan region 12 in FIG. 1A is at the retina, and the z-scan location of scan region 12 in FIG. 1A is at the floater.

Figure 2C:
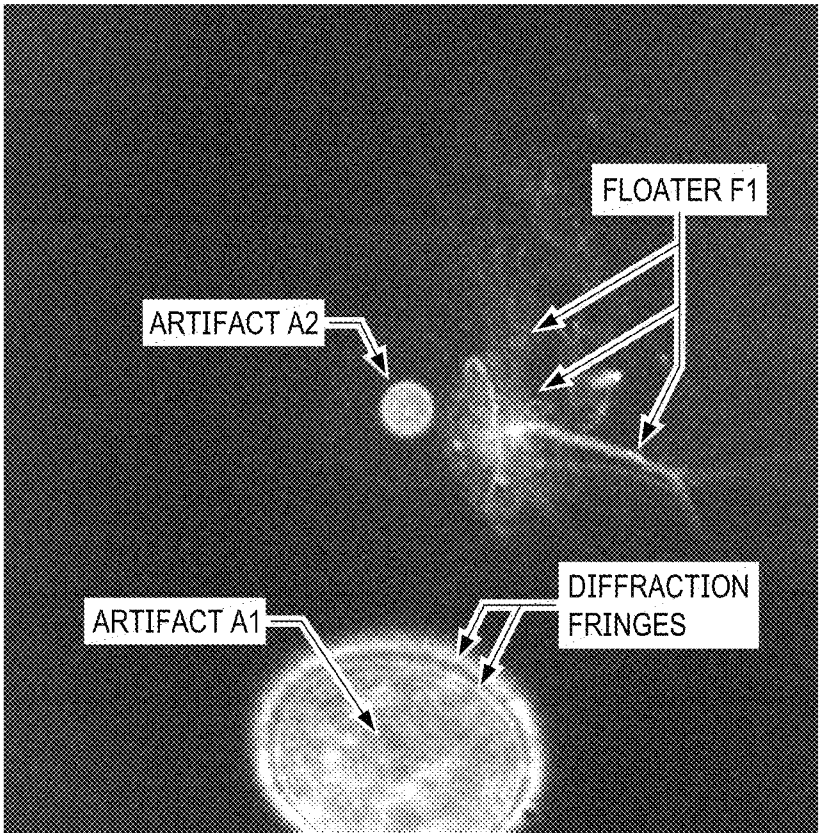

In FIGS. 1A and 2A, scan region 12 is located at the retina. FIG. 2A shows shadows S1 and S2 that floaters cast on the retina. In FIGS. 1B, 2B, and 2C, scan region 12 is located at a floater F1.

In FIG. 2B, since scan region 12 is located at floater F1, floater F1 appears as a bright, sharp, two-dimensional enface object moving within the image frame. Floater F2 is near, but not at, the focus of the SLO beam, so appears darker and blurrier than floater F1. In general, the shape of a floater should resemble the shape of the corresponding floater shadow. Artifact A1 is a first Purkinje image caused by a reflection from the anterior surface of the cornea. Artifact A1 includes diffraction fringes around the edge of the first Purkinje image. Artifact A2 is caused by reflections from optical components (such as L1, L2, L3, L4, and/or L5).

In FIG. 2C, floater F1 is a large, diffuse floater at the focal point of the SLO beam. Since scan region 12 is located at floater F1, floater F1 appears as a bright, sharp, two-dimensional enface object moving within the image frame. As described above, artifact A1 is a first Purkinje image, and artifact A2 is caused by reflections from optical components.

Figure 3:
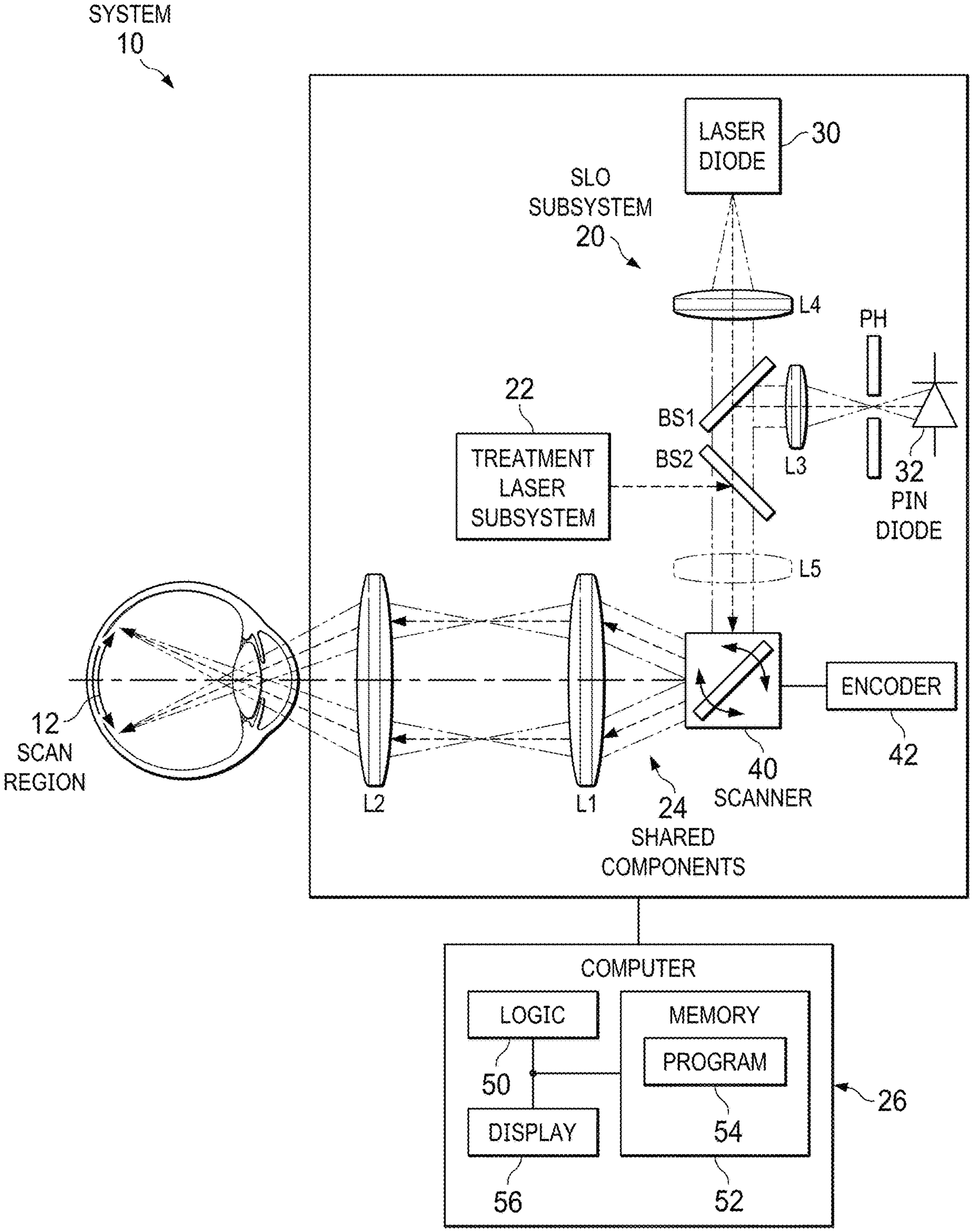
FIG. 3 illustrates an example of an ophthalmic surgical laser system that may be used to treat a floater in an eye, according to certain embodiments.

FIG. 3 illustrates an example of an ophthalmic surgical laser system 10 that may be used to image and treat a floater in an eye, according to certain embodiments. As an overview, system 10 includes a scanning laser ophthalmoscope (SLO) subsystem 20, a treatment laser subsystem 22, one or more shared components 24, and a computer 26, coupled as shown. SLO subsystem include a laser source (e.g., laser diode 30), optical elements (such as lenses L3, L4, and/or L5, and beamsplitters BS1 and BS2), a pinhole filter PH, and a PIN diode 32, coupled as shown. Shared components 24 include a scanner (e.g., an xy- or 2D scanner) 40, an xy-encoder 42, and optical elements (such focusing lenses L1 and L2, where L2 may be an objective lens), coupled as shown. Computer 26 includes logic 50, a memory 52 (which stores a computer program 54), and a display 56, coupled as shown. System 10 may include a sensor (e.g., an ultrasonic sensor) that monitors the position of the patient's eye and/or head relative to a system component (e.g., objective lens L2). In general, an optical element can act on (e.g., transmit, reflect, refract, diffract, collimate, condition, shape, focus, modulate, and/or otherwise act on) a laser beam.

According to an overview of an example of imaging, e.g., the retina or a floater, an SLO laser source (e.g., laser diode 30) of SLO subsystem 20 provides an SLO laser beam with an SLO focal point. Lens L4 collimates the SLO laser beam. The SLO laser beam passes through beamsplitters BS1 and BS2, is deflected by scanner 40, passes through lenses L1 and L2 (and L5 in certain embodiments), and is focused onto, e.g., the retina or a floater. That is, beamsplitter BS1 passes the SLO laser beam through towards beamsplitter BS2, and beamsplitter BS2 passes the beam through towards scanner 40. (In certain embodiments, tunable lens L5 passes the SLO laser beam through.) Scanner 40 scans the SLO laser beam across a scan region within the eye. Focusing lenses L1 and L2 image scanner 40 into the pupil to focus the SLO and treatment laser beams to a common focal point to form the scan region at the z-scan location of, e.g., the retina or a floater, which reflects back the light. In this way, a large angular range of the retina can be scanned with the SLO beam.

Continuing with the example overview, the reflected light travels back through lenses L1, L2, scanner 40, (lens L5 in certain embodiments), and beamsplitter BS2. Beamsplitter BS1 directs the reflected beam towards lens L3, which focuses the beam onto confocal pinhole filter PH. Pinhole filter PH directs the beam to PIN diode 32. The position of pinhole filter PH is optically conjugated to the focal point of the SLO laser beam, so only light reflected back from the focal point of the SLO beam is detected by PIN diode 32 and all other back reflections are suppressed by pinhole filter PH. PIN diode 32 outputs a signal proportional to the intensity of the detected light, which can be used to generate an image of the floater.

Continuing with the example overview, computer 26 gathers the signal from PIN diode 32 and the angular deflections of the beams from xy-encoder 42 and generates an image of the reflected light as a function of the xy-readings from xy-encoder 42. If system 10 is imaging and treating a floater in the vitreous, optical elements are positioned to aim the SLO and treatment laser beams the z-location of the floater. The floater image is sharper and brighter while the background is darker because pinhole filter PH allows backscattered light from the floater through to PIN diode 32 and suppresses backscattered light from the retina. Computer 26 determines the xy-location of the floater, and instructs treatment laser subsystem 22 to generate the treatment laser beam and scanner 40 to aim the beam at the xy-location of the floater. Beamsplitter BS1 directs the treatment laser beam to optical elements that direct the beam to the z-scan location of the floater to destroy the floater.

Turning to the parts of the system, SLO subsystem 20 utilizes confocal laser scanning to generate images of the interior of the eye. SLO subsystem 20 moves scan region 12 of SLO focal point in the z-direction to gather light at different z-scan locations, e.g., from the retina and through the vitreous. Pinhole filter PH is optically conjugated to the SLO focal point such that only the light from the SLO focal point is detected by PIN diode 32 and the other light (e.g., reflections from the cornea or lens) is suppressed. SLO subsystem 20 plots the intensity of the back reflected light as a function of the xy-position of the focal point to generate an SLO image.

Treatment laser subsystem 22 generates a laser beam with any suitable wavelength, e.g., in a range from 350 nm to 2000 nm. Treatment laser subsystem 22 delivers laser pulses at any suitable repetition rate (e.g., a single pulse to 200 megahertz (MHz)). A laser pulse has any suitable pulse duration (e.g., 20 femtoseconds (fs) to 1000 nanoseconds (ns)), any suitable pulse energy (e.g., 1 nanojoule (nJ) to 10 millijoule (mJ) or an energy that exceeds the optical breakdown threshold of the vitreous), and a focal point of any suitable size (e.g., 1 to 30 microns). The treatment laser beam is collimated to spatially coincide with the SLO beam such that the focal points of the SLO beam and the treatment laser beam precisely spatially coincide, i.e., the beams are focused at the same spot.

In certain embodiments, treatment laser subsystem 22 directs a laser pulse at the floater to destroy the floater. In other embodiments, treatment laser subsystem 22 directs a plurality of laser pulses that form a three-dimensional (3D) volume. The geometric center of the 3D volume may be substantially aligned with the geometric center of the floater, and the 3D volume may cover all or almost all, such as 80% or more of the volume of the floater. In the embodiments, scanner 40 scans the pulses in the xy-directions, and, e.g., tunable lens L5 scans the focus in the z-direction.

Shared components 24 direct beams from SLO subsystem 20 and treatment laser subsystem 22, towards the eye. Because SLO and laser beams share components 24, the beams are affected by the same geometrical distortions (e.g., fan distortion of scanners, barrel or pillow distortions of the scanner lens, refractive distortions from the inner eye surfaces, and other distortions). The distortions affect the beams in the same way, so the beams propagate along the same path. This allows for aiming the laser beam precisely at the floater. Shared components 24 may also provide spectral and/or polarization coupling and/or decoupling of the SLO and laser beams to allow the beams to share the same path.

Turning to the details of shared components 24, scanner 40 may be any suitable xy-scanner that changes the angle of incidence of a beam into the pupil to angularly direct the focal point of the beam in the x- and y-directions. Scanner 40 may include, e.g., a pair of galvanometrically-rotated scanner mirrors that can be tilted about mutually perpendicular axes; an acousto-optical crystal that can acousto-optically steer the beam; and/or a fast scanner (e.g., a galvanometric, resonant, or acousto optical scanner) that can create, e.g., a two-dimensional matrix of laser spots of the treatment laser beam.

Xy-encoder 42 detects the angular position of xy-scanner 40 and reports the position as the xy-location measured in encoder units, e.g., angular units. For example, xy-encoder 42 detects the angular orientations of the galvanometer mirrors of xy-scanner 40 and records the orientations as encoder units. Xy-encoder 42 may report the position in encoder units to SLO subsystem 20, treatment laser subsystem 22, and/or computer 26. Since both SLO subsystem 20 and treatment laser subsystem 22 share the same xy-scanner 40, computer 26 can use the encoder units to instruct subsystems 20, 22 where to aim their beams, making it unnecessary to perform the computer-intensive conversion from encoder units to a length unit such as millimeters. Xy-encoder 42 reports the positions at any suitable rate, e.g., once every 5 to 50 milliseconds (ms), such as every 10 to 30 or approximately every 20 ms.

Lenses L1 and L2 image scanner 40 into the pupil to allow the SLO and treatment laser beams to scan a wide angular range. Lenses L1 and L2 include any suitable number of lenses arranged in any suitable manner to image scanner 40 into the pupil while allowing system 10 to change the convergence angle (i.e., the diopter number) of the beam entering the pupil. The diopter can be increased to shift the focus of the SLO beam into the vitreous.

Computer 26 controls components of system 10 (e.g., SLO subsystem 20, laser device 24, and/or shared components 24) in accordance with a computer program 54. Computer 26 may be separated from components or may be distributed among system 10 in any suitable manner, e.g., within SLO subsystem 20, laser device 24, and/or shared components 24. In certain embodiments, portions of computer 26 that control SLO subsystem 20, laser device 24, and/or shared components 24 may be part of SLO subsystem 20, laser device 24, and/or shared components 24, respectively.

Computer 26 controls the components of system 10 in accordance with a computer program 54. Examples of computer programs 54 include object imaging, object tracking, image processing, image analysis, floater evaluation, and retinal exposure calculation programs. For example, computer 26 uses a computer program 54 to instruct SLO subsystem 20, laser device 24, and/or shared components 24 to: move the scan region to a floater such that the SLO and treatment focal points are aimed at the floater; generate an image of the floater; determine the xy-location of the floater; and/or direct the treatment laser beam towards the floater.

In certain embodiments, computer 26 uses an image analysis program 54 to analyze the digital information of images. For example, computer 26 analyzes images using, e.g., edge detection or pixel analysis, to look for shapes that could be floaters and differentiate between floater and non-floater images. Computer 26 may identify a darker shape on the retina moving relative to the vasculature as a floater shadow and a lighter shape in the vitreous as a floater. An opacity that moves with the vasculature may be recognized by computer 26 as an anatomical opacity of the retina, not a floater.

In addition, computer 26 may recognize certain images as artifacts, as shown in FIGS. 2B and 2C. A large, bright patch with diffraction fringes around the edge that moves in the opposite direction of the SLO image within the display frame (e.g., downwards when the image moves upwards in the display frame or to the left when the image moves to the right) may be a first Purkinje image, as shown as artifact A1 of FIGS. 2B and 2C. A bright spot that does not move relative to the SLO display frame may be an internal reflection from optical components (such as L1, L2, L3, L4, and/or L5), as shown as artifact A2 of FIGS. 2B and 2C.

As another example of using image analysis program 54, computer 26 analyzes the image of a floater shadow to determine if the shadow is cast by a significant floater, e.g., a clinically significant floater that should be treated. The shape and size of the floater shadow indicates the size and shape of the floater, and the tone or luminance of the floater shadow indicates the density of the floater. As another example, computer 26 analyzes the image of a floater to determine if the SLO focal point is focused on the floater. If the edges of floater are sharp, i.e., the floater is in focus, the focal point at or near the floater. If the floater image is the brightest when focusing the SLO beam in z direction and the sharpest, then the floater is at the focus of the SLO beam.

In certain embodiments, computer 26 generates images to be presented on display 56. For example, computer 26 presents multiple successive images as a video. As another example, computer 26 combines multiple SLO images taken a different z-scan locations into a three-dimensional (3D) image. The 3D image may be used to determine the spatial size and location of an array of laser treatment pulses used to treat a floater.

In certain embodiments, computer 26 determines the xy-location of the floater. For example, computer 26 may receive user input indicating the xy-location of the floater. The user may input the xy-location by selecting the xy-location on a displayed image that corresponds to the location of the floater, e.g., by touching the xy-location on a screen or by selecting the xy-location with a cursor. In other embodiments, computer 26 may perform image analysis on an SLO image to determine the xy-location of the floater. Computer 26 may identify the floater in the image and then determine the xy-location from the location in the image. After computer 26 determines the xy-location of the floater, computer 26 may instruct scanner 40 to direct a treatment beam to the floater location in encoder units.

In certain embodiments, computer 26 calculates the radiation exposure on the retina from a laser pulse directed towards a location, e.g., the location of a floater, and performs an alarm response if the retinal exposure exceeds a predetermined limit. For example, the retinal exposure EXP can be calculated as $EXP=[E/(L*\alpha)^2\pi/4]$ where E is the laser pulse energy, $\alpha$ is the full convergence angle of the laser beam in the vitreous focused on the location of the floater, and L is the distance to the retina, e.g., the floater-to-retina distance, which can be calculated as described below. The radiant exposure should be less than a maximum radiant exposure, which may be determined in accordance with accepted standards. For example, the maximum radiant exposure may be set in accordance with ANSI Z80.36-2016 Maximum Permissible Exposure (ANSI MPE). If the radiant exposure exceeds the maximum radiant exposure, e.g., the ANSI MPE, computer 26 may perform an alarm response, such as modify any suitable factor (e.g., lower the pulse energy), provide a notification to the user, and/or prevent firing of the laser beam. Computer 26 may also calculate an exposure ratio R=EXP/[ANSI MPE] and provide ratio R to the user (e.g., surgeon) to allow the user to determine whether to treat the floater.

Display 56 may be any suitable hardware that can display an image. Examples of display 56 include a computer monitor and virtual reality glasses. A user (e.g., a surgeon or other medical personnel) at the surgery site or remote from the site may view images generated by the computer.

Involuntary and voluntary eye movements (e.g., saccadic and microsaccadic movements, drift, and tremor) can make laser treatment difficult. To reduce movement, the eye may be stabilized. For example, the treated eye and/or other eye may be stabilized with a fixation light. If the xy-position of the fixation light can be moved up to 25 degrees in any angular direction, floaters located far from the visual axis can be treated. As another example, a patient interface or handheld surgical contact lens may be used to mechanically stabilize the eye. The interface or lens may have a spherical contact surface that reduces refractive error of the eye, such as corneal astigmia and asphericity of the eye. As another example, movement of the floater may be tracked by tracking software, and the focus of the treatment laser may continuously be aimed at the moving floater.

2. Examples of Moving the Focal Point

Figure 4:
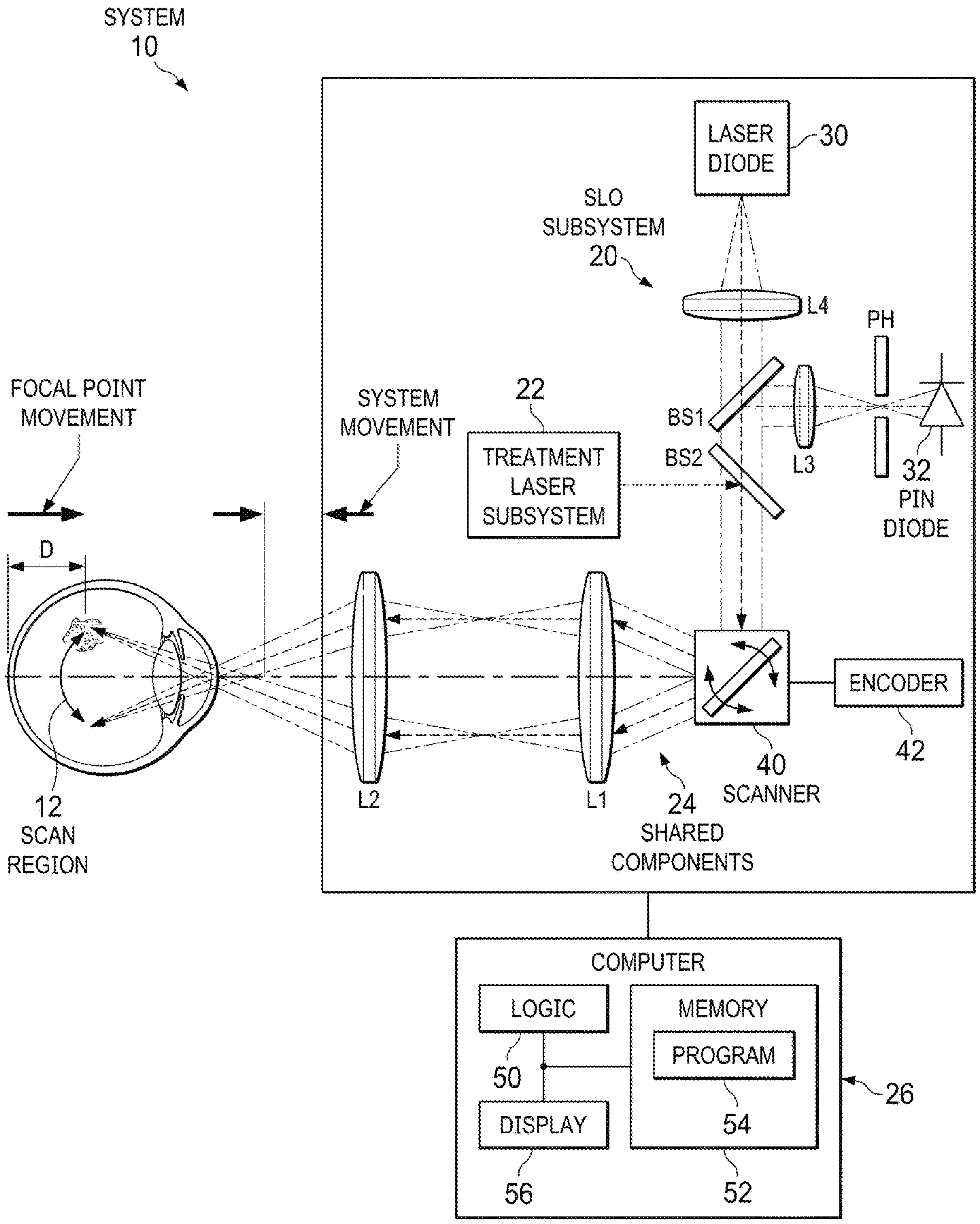
FIG. 4 illustrates an example of how an ophthalmic surgical laser system can move a scan region, according to certain embodiments.
Figure 5:
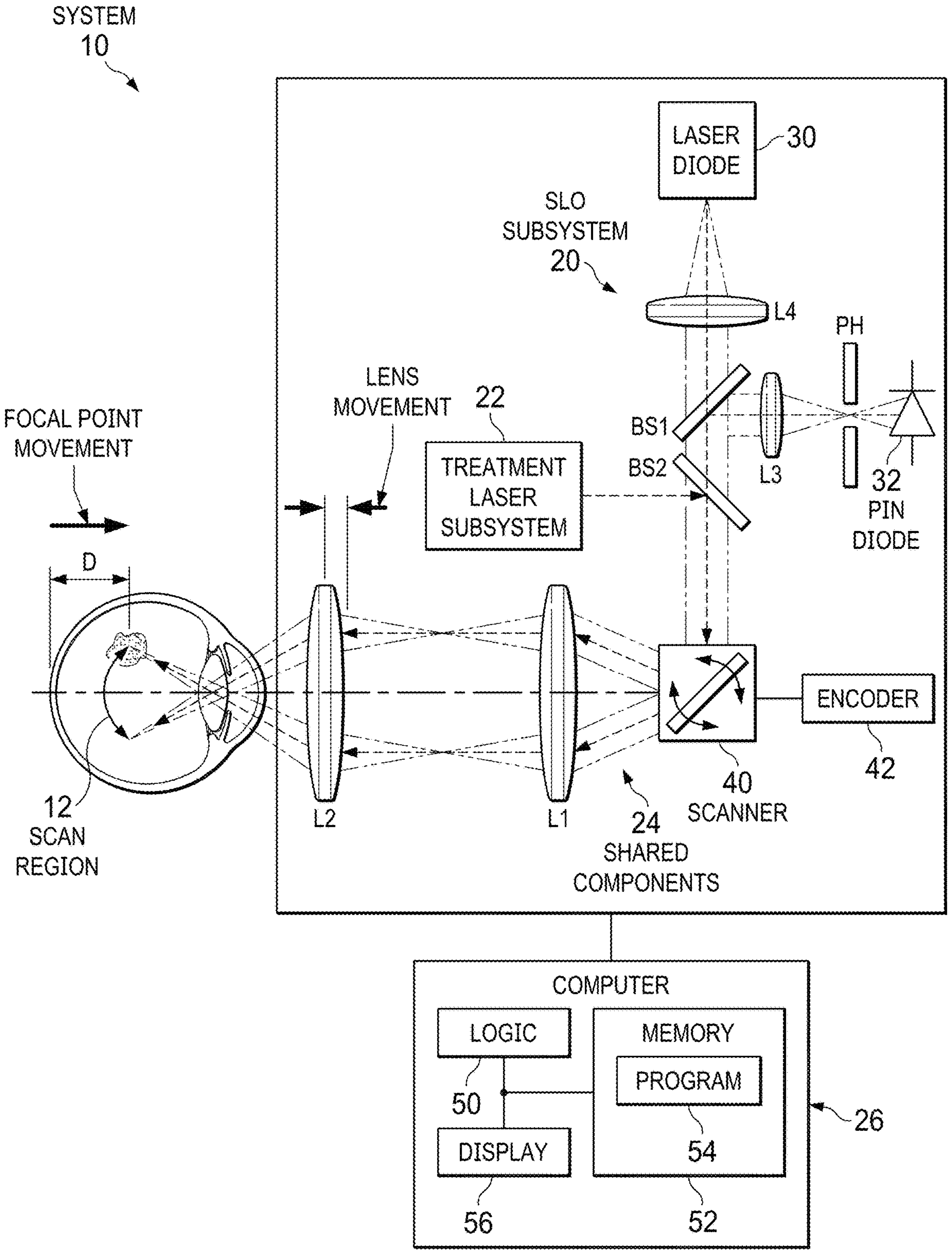
FIG. 5 illustrates another example of how an ophthalmic surgical laser system can move a scan region, according to certain embodiments.
Figure 6:
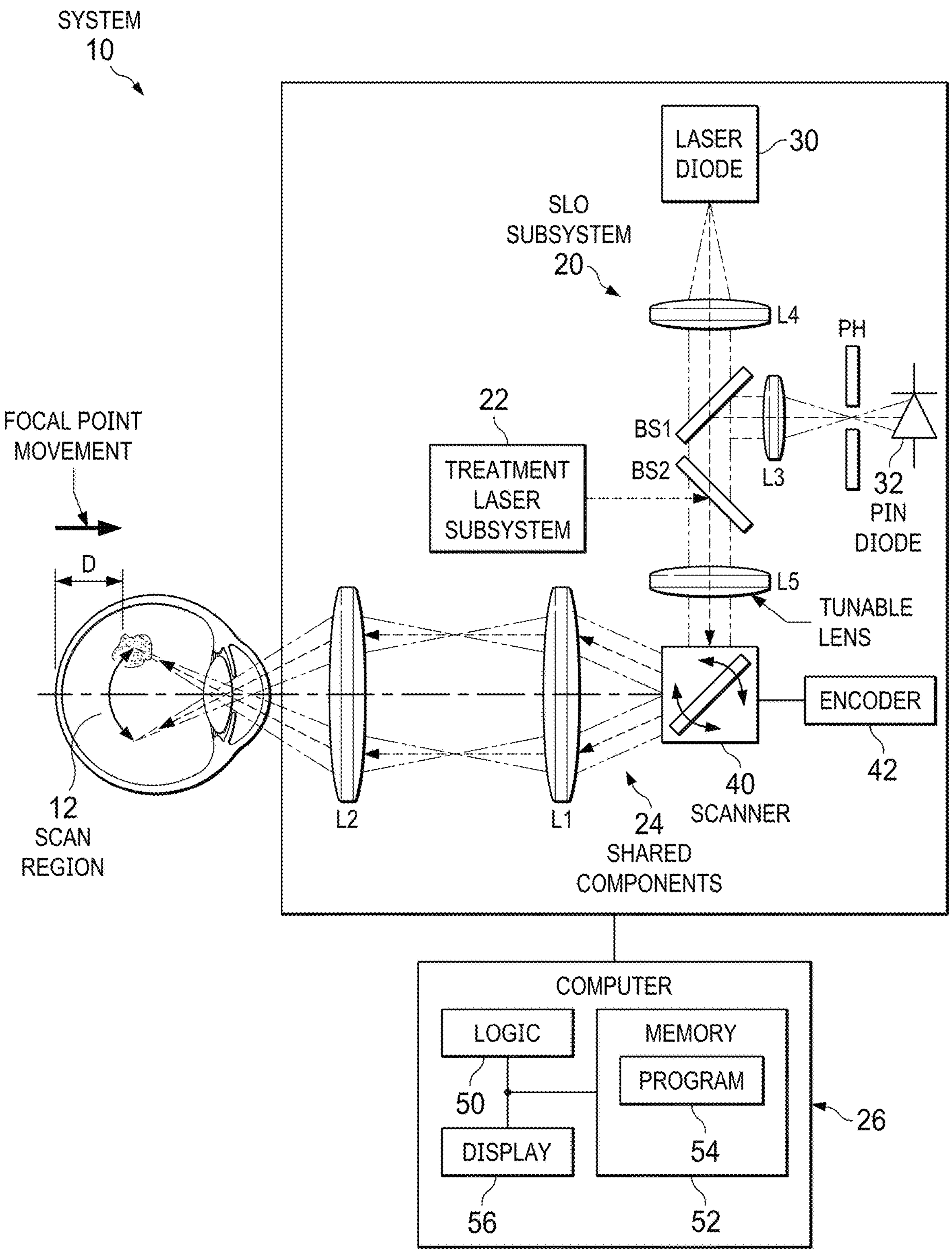
FIG. 6 illustrates yet another example of how an ophthalmic surgical laser system can move a scan region, according to certain embodiments.

FIGS. 4 through 6 illustrate embodiments of ophthalmic surgical laser system 10 that can move the image and treatment focal points in the z-direction, and FIGS. 8A through 8C illustrate examples of images taken at different z-scan locations. In certain embodiments, components of system 10 are adjusted (e.g., moved, reshaped, or otherwise modified) to move scan region 12. The components may be adjusted in any suitable manner. For example, a mechanical structure can apply force to move a component in response to a user action; a motorized actuator can move a component; and/or an electrical current can reshape or otherwise modify a tunable lens. The movement may be initiated in response to, e.g., a user moving a controller (such as a knob) and/or a command from computer 26.

From the changes system 10 makes to adjust scan region 12 from the retina to a floater, computer 26 can calculate the distance between the retina and floater ("floater-to-retina distance"). For example, the floater-to-retina distance may be calculated from the distance components of system 10 move to adjust scan region 12 or the difference in diopters needed to adjust scan region 12, as described in more detail below. Computer 26 may use a mathematical function or a lookup table that describes the relationship between the floater-to-retina distance and the system changes (e.g., between the floater-to-retina distance and the distance components move to adjust scan region 12 or between the floater-to-retina distance and the difference in diopters needed to adjust scan region 12) to calculate the distance. The function or lookup table may be generated in any suitable manner. For example, during calibration or manufacture of system 10, the z-scan location can be recorded for different component locations or diopters, and the function or table can be determined from the results. As another example, the function or table may be determined from an eye model, such as a Zemax eye model. In certain embodiments, the floater-to-retina distance can be used to calculate the potential retinal radiation exposure from a laser beam directed towards the floater, as described above.

FIG. 4 illustrates an example of how ophthalmic surgical laser system 10 can move scan region 12, according to certain embodiments. In the embodiments, computer 26 or the user moves scan region 12 by moving, relative to the eye, the optical elements that produce scan region 12, e.g., SLO subsystem 20, treatment laser subsystem 22, and/or shared components 24 (such as scanner 40 and focusing lenses L1, L2). The components may be mechanically coupled such that they move together in the z-direction relative to the base of system 10, e.g., a table base. In the embodiments, the eye is stabilized relative to the base, such that the movement (i.e., the change in z-location) of the components relative to the base represents movement M relative to the eye. Linear encoder 42 may record the relative movement M and report the relative movement M to computer 26 in encoder units.

In certain embodiments, computer 26 calculates the floater-to-retina distance F from the relative movement M. For example, each unit of relative movement M changes the z-scan location of scan region 12 by n units, where n is the refractive index of the vitreous, 1.34. Thus, floater-to-retina distance F is approximately $F=1.34 \times M$. As another example, during calibration of system 10, the z-scan location is recorded for different locations of the moving components, and a function or table is calculated from the results. Computer 26 uses the function or table to calculate the floater-to-retina distance F.

FIG. 5 illustrates another example of how ophthalmic surgical laser system 10 can move scan region 12, according to certain embodiments. In certain embodiments, computer 26 moves the scan region by changing the relative distance between focusing lenses L1 and L2 to move the SLO and treatment laser focal points.

In certain embodiments, system 10 describes this change as a change in diopter D. In the embodiments, computer 26 calculates the floater-to-retina distance F from the change in diopter ΔD. For example, for the average human eye, each +1-diopter change ΔD in the convergence of the laser beam corresponds to a F=0.36 mm shift of scan region 12 away from the retina. Thus, floater-to-retina distance $F=0.36 \times \Delta D$ mm. The 0.36 multiplier works in the vicinity of the retina, and lookup table or mathematical function may be generated, as described above, for larger distances.

FIG. 6 illustrates yet another example of how ophthalmic surgical laser system 10 can move scan region 12, according to certain embodiments. In certain embodiments, system 10 includes a tunable lens L5 that moves the SLO and treatment laser focal points in the z-direction. In the embodiments, computer 26 moves the scan region by adjusting the tunable lens L5 to convert the collimated laser beam to a convergent laser beam that forms the focal points. Tunable lens L5 may be any suitable lens or arrangement of lenses. For example, tunable lens L5 may be an electrically tunable lens, which may yield fast scanning of the focal points. As another example, tunable lens L5 may be a compound lens comprising two or more lenses. Adjusting the distance between the lenses changes the equivalent refractive power. In certain embodiments, system 10 describes this adjustment as a change in diopter D, and computer 26 calculates the floater-to-retina distance F from the change in diopter ΔD, as described above.

Figure 7A:
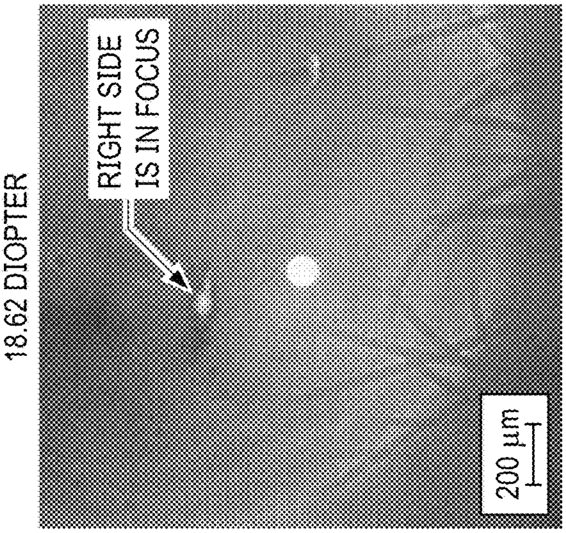
FIGS. 7A to 7C illustrate examples of images of a floater that were generated at different z-scan locations.
Figure 7B:
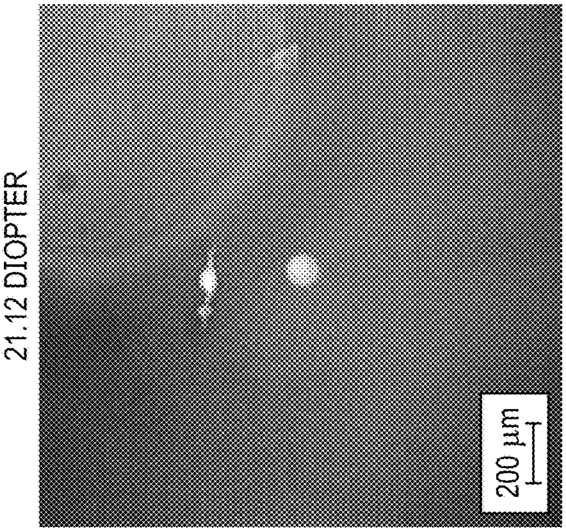
Figure 7C:
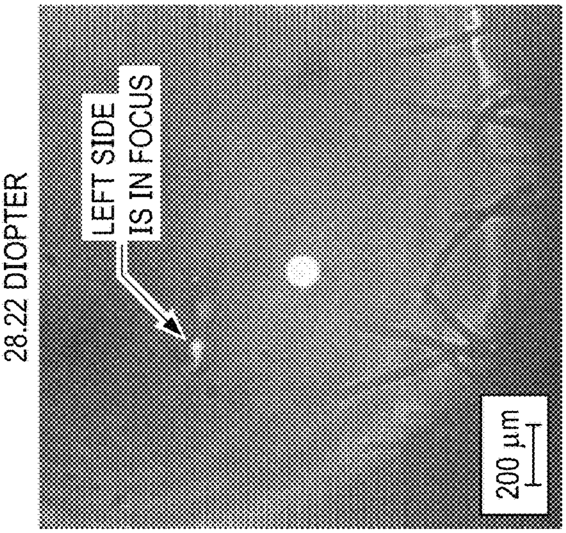

FIGS. 7A to 7C illustrate examples of images of the same floater that may be generated at different z-scan locations. In the images, different parts of the floater are in focus at different z-scan locations. FIG. 7A shows the scan region at 18.6 D, or 6.7 mm from the retina, where the right side of the floater is in focus. FIG. 7B shows the scan region at 21.2 D, or 7.6 mm, where the center is in focus. FIG. 7C shows the scan region at 28.2 D, or 10.1 mm, where the right side is in focus.

3. Example Method

Figure 8:
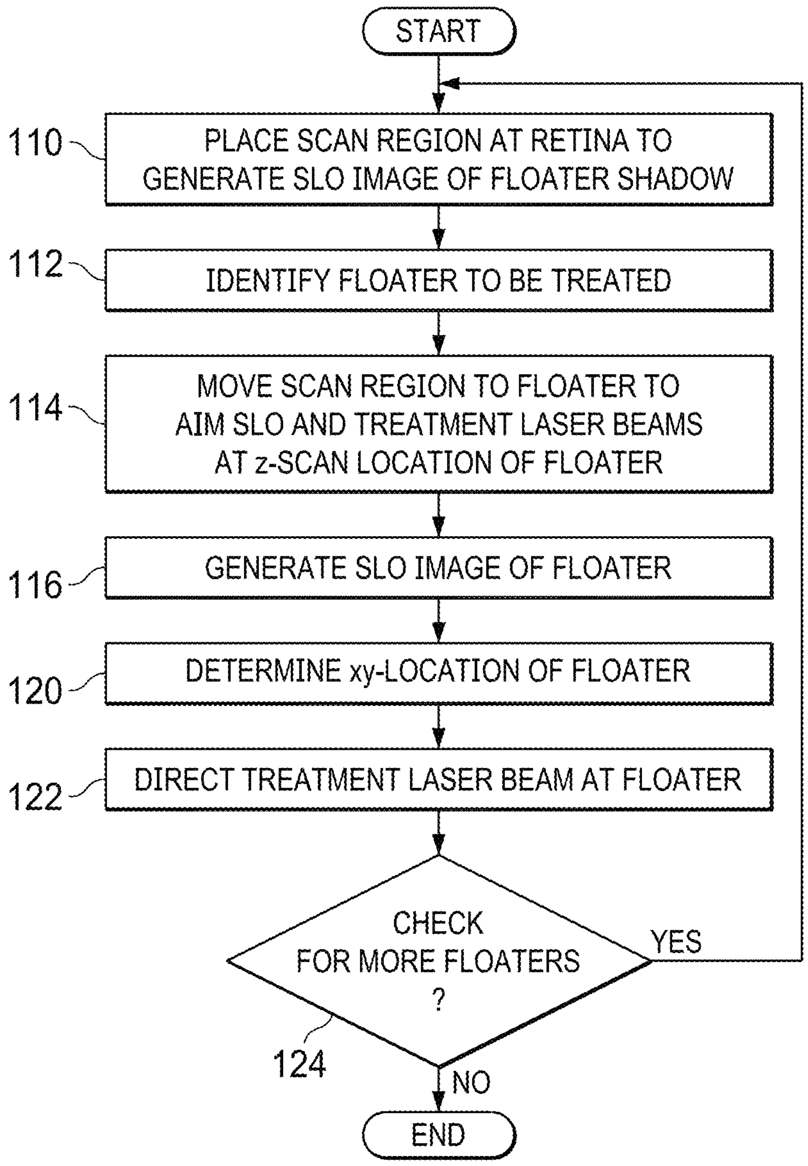
FIG. 8 illustrates an example of a method for treating a floater that may be used by the system of FIG. 1, according to certain embodiments.

FIG. 8 illustrates an example of a method for treating a floater that may be used by system 10 of FIG. 1, according to certain embodiments. Certain steps of the method may be performed by the computer of the system instructing system components to perform the steps. During the method in certain embodiments, the computer may calculate a retinal radiation exposure of the treatment laser beam on the retina. If the retinal radiation exposure exceeds a predetermined limit, the computer may perform an alarm response (e.g., notify the user and/or stop the treatment).

The method starts at step 110, the scan region is placed at the retina to generate an SLO image of a floater shadow on the retina. The computer or user may adjust (e.g., move) optical elements that produce the scan region to place the scan region to the retina. The scanner of the system may perform an angular scan around the visual axis larger than, e.g., 45 degrees, to detect floater shadows. The floater to be treated is identified at step 112. In certain embodiments, the computer may analyze an image of the floater shadow to determine if the floater may be graded as clinically significant according to, e.g., the size, density, and/or xy-location of the floater shadow. In other embodiments, the user (e.g., a surgeon) may determine if the floater is significant.

The scan region is moved to the floater to aim the SLO and treatment laser beams towards the z-scan location of the floater at step 114. The computer or user may adjust optical elements that produce the scan region in order to move the scan region. The optical element may be adjusted by, e.g., moving one or more of the optical elements, changing the relative distance between focusing lenses of the focal points, and/or adjusting a tunable lens that moves the focal points. When the scan region is at the floater, the image of the floater is bright and sharp because the focal points of the SLO and the treatment laser beams are at the floater. The brightness and sharpness can be evaluated by the user or by the computer using an image analysis program.

the floater is in focus. In certain embodiments, the computer may analyze an image of the floater to determine if the floater is in focus. In other embodiments, the user may determine if the floater is in focus.

The SLO subsystem generates an SLO image of the floater at step 116. In certain embodiments, the SLO subsystem generates a plurality of images at different z-locations, and the computer generates a three-dimensional image from the plurality of images. The computer determines the xy-location of the floater at step 120. The xy-location may be determined by analyzing the SLO image of the floater in the vitreous.

The treatment laser subsystem directs a treatment laser beam towards the floater at step 122. For example, the treatment laser subsystem directs a laser pulse towards the floater. As another example, the treatment laser subsystem directs laser pulses that form a three-dimensional volume. The treatment laser subsystem substantially aligns the geometric center of the three-dimensional volume with the geometric center of the floater. The user may want to check for more floaters at step 124. If so, the method returns to step 110, where the scan region is placed at the retina to generate an SLO image of the retina to check if there are any more floater shadows, indicating the presence of floaters. If not, the method ends.

A component (such as control computer 26) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic surgical laser system for treating a floater in a vitreous of an eye, the eye having a retina, the system comprising:

a scanning laser ophthalmoscope (SLO) subsystem comprising:
- an SLO laser source configured to provide an SLO laser beam with an SLO focal point; and
- a pinhole filter conjugated to the SLO focal point;

a treatment laser subsystem configured to provide a treatment laser beam with a treatment focal point, the treatment focal point spatially coinciding with the SLO focal point;

a scanner configured to:
- scan the SLO laser beam across a scan region; and
- direct the treatment laser beam to an xy-location of the scan region;

a plurality of optical elements comprising a plurality of focusing lenses, the optical elements configured to:
- aim the SLO laser beam and the treatment laser beam at substantially the same point of the scan region;
- focus the SLO focal point to form the scan region at a z-scan location;
- move the scan region in a z-direction to the z-scan location of the floater; and
- focus the treatment focal point at the z-scan location of the floater; and a computer configured to:
- receive and analyze an image of a shadow of the floater on the retina from the SLO subsystem;
- determine whether the floater is clinically significant based on one or more characteristics of the floater derived from the analysis of the image of the shadow, the characteristics comprising at least one a size, shape, tone, luminance, density, location, or sharpness of the floater; and
- if the floater is clinically significant:
  - determine an xy-location of the floater; and
  - instruct the treatment laser subsystem to direct the treatment laser beam towards the xy-location and the z-scan location of the floater.

2. The ophthalmic surgical laser system of claim 1, the optical elements configured to move the scan region in the z-direction by:

changing a relative distance between the eye and at least one of the plurality of optical elements.

3. The ophthalmic surgical laser system of claim 1, the optical elements configured to move the scan region in the z-direction by:

changing a relative distance between the plurality of focusing lenses.

4. The ophthalmic surgical laser system of claim 1, the optical elements:

further comprising a tunable lens configured to move the SLO focal point and the treatment focal point; and configured to move the scan region in the z-direction by adjusting the tunable lens to move the SLO focal point and the treatment focal point in the z-direction.

5. The ophthalmic surgical laser system of claim 1, the computer configured to direct the SLO focal point to the xy-location of the floater by:

receiving user input indicating the xy-location of the floater.

6. The ophthalmic surgical laser system of claim 1, the computer configured to determine the xy-location of the floater by:

analyzing the image of the floater from the SLO subsystem; and determining the xy-location of the floater from the image.

7. The ophthalmic surgical laser system of claim 1:

the optical elements configured to move the scan region to the retina of the eye; and the SLO subsystem configured to generate an image of a shadow of the floater on the retina.

8. The ophthalmic surgical laser system of claim 1, the treatment laser subsystem configured to direct the treatment laser beam towards the xy-location and the z-scan location of the floater by:

directing a plurality of laser pulses at the floater.

9. The ophthalmic surgical laser system of claim 1, the treatment laser subsystem configured to direct the treatment laser beam towards the xy-location and the z-scan location of the floater by:

directing a plurality of laser pulses towards the floater, the plurality of pulses forming a three-dimensional volume, the three-dimensional volume covering 80% or more of a volume of the floater.

10. The ophthalmic surgical laser system of claim 1, the computer configured to:

analyze an image of the floater from the SLO subsystem; and determine whether the floater is in focus.

11. The ophthalmic surgical laser system of claim 1, the computer configured to:

calculate a floater-to-retina distance according to changes in the system used to adjust the scan region between the retina and the floater.

12. The ophthalmic surgical laser system of claim 11, the computer configured to:

calculate the floater-to-retina distance according to a distance a plurality of system components move to adjust the scan region between the retina and the floater.

13. The ophthalmic surgical laser system of claim 11, the computer configured to:

calculate the floater-to-retina distance according to a difference in diopters used to adjust the scan region between the retina and the floater.

14. The ophthalmic surgical laser system of claim 1, the computer configured to:

calculate a retinal radiation exposure of the treatment laser beam focused at the z-scan location of the floater; and perform an alarm response if the retinal radiation exposure exceeds a predetermined limit.

15. The ophthalmic surgical laser system of claim 14, the computer configured to calculate the retinal radiation exposure EXP according to $EXP=[E/(L*\alpha)^2\pi/4]$, where E represents a laser pulse energy, $\alpha$ represents a full convergence angle of the treatment laser beam focused at the z-scan location of the floater, and L represents a floater-to-retina distance calculated according to the z-scan location of the floater.

16. The ophthalmic surgical laser system of claim 1, the computer configured to track movement of the floater using tracking software.

17. The ophthalmic surgical laser system of claim 1:

the SLO subsystem configured to generate a plurality of images of the eye at different z-scan locations; and the computer configured to generate a three-dimensional image from the plurality of images.

18. The ophthalmic surgical laser system of claim 1, further comprising a display, the display comprising a computer monitor or virtual reality glasses.

19. The ophthalmic surgical laser system of claim 1, the treatment laser beam having a wavelength in a range of 350 nanometers (nm) to 2000 nm and laser pulses with pulse durations in a range of 20 femtoseconds (fs) to 1000 nanoseconds (ns).

20. The ophthalmic surgical laser system of claim 1, further comprising an ultrasonic sensor configured to monitor a position of the eye relative to an objective lens of the plurality of optical elements.

21. A method for treating a floater in a vitreous of an eye, the eye having a retina, the method comprising:

providing, by a scanning laser ophthalmoscope (SLO) subsystem, an SLO laser beam with an SLO focal point;

providing, by a treatment laser subsystem, a treatment laser beam with a treatment focal point, the treatment focal point spatially coinciding with the SLO focal point;

scanning, by a scanner, the SLO laser beam across a scan region;

aiming, by a plurality of optical elements, the SLO laser beam and the treatment laser beam at substantially the same point of the scan region;

focusing, by the optical elements, the SLO focal point to form the scan region at a z-scan location;

moving, by the optical elements, the scan region to the z-scan location of the floater;

receiving and analyzing, by a computer, an image of a shadow of the floater on the retina from the SLO subsystem;

determining if the floater is clinically significant based on one or more characteristics of the floater derived from the analysis of the image of the shadow, the characteristics comprising at least one of a size, shape, tone, luminance, density, location, or sharpness of the floater; and if the floater is clinically significant:

determining, by the computer, an xy-location of the floater;

instructing, by the computer, the treatment laser subsystem to direct the treatment laser beam towards the xy-location and the z-scan location of the floater;

directing, by the scanner, the treatment laser beam to an xy-location of the scan region; and focusing, by the optical elements, the treatment focal point at the z-scan location of the floater.

22. The method of claim 21, the moving the scan region to the z-scan location comprising:

changing a relative distance between the eye and at least one of the plurality of optical elements.

23. The method of claim 21, the moving the scan region to the z-scan location comprising:

changing a relative distance between a plurality of focusing lenses.

24. The method of claim 21, the moving the scan region to the z-scan location comprising:

adjusting a tunable lens to move the SLO focal point and the treatment focal point.

* * * * *